United States Patent [19]

Hebrank et al.

[11] Patent Number: 5,745,228
[45] Date of Patent: Apr. 28, 1998

[54] METHOD AND APPARATUS FOR DISTINGUISHING LIVE FROM INFERTILE POULTRY EGGS

[75] Inventors: John Hebrank, Durham; Daniel De Pauw, Raleigh, both of N.C.

[73] Assignee: Embrex, Inc., Research Triangle Park, N.C.

[21] Appl. No.: 785,689

[22] Filed: Jan. 17, 1997

[51] Int. Cl.[6] .................................................. G01N 33/08
[52] U.S. Cl. ............................................. 356/53; 250/341.1
[58] Field of Search ................................ 250/341.1, 350, 250/358.1, 340; 356/52–53

[56] References Cited

U.S. PATENT DOCUMENTS

| | | | |
|---|---|---|---|
| 3,540,824 | 11/1970 | Fonda et al. | 356/53 |
| 4,671,652 | 6/1987 | van Asselt et al. | 356/66 |
| 4,914,672 | 4/1990 | Hebrank | 374/124 |
| 4,955,728 | 9/1990 | Hebrank | 374/124 |
| 4,978,225 | 12/1990 | Reimer | 356/432 |
| 5,017,003 | 5/1991 | Keromnes et al. | |
| 5,321,491 | 6/1994 | Summers et al. | 356/53 |

FOREIGN PATENT DOCUMENTS 969581  9/1964  United Kingdom .

OTHER PUBLICATIONS

K. Das et al.; Detecting Fertility of Hatching Eggs Using Machine Vision I. Histogram Characterization Method, *Transactions of the ASAE* 35(4):1335–1441 (1992).

Product Brochure; EPM 650 Automatic Candling and Transfer Machine, Innovatec, date not available, page Nos. not available.

*Primary Examiner*—Frank G. Font
*Assistant Examiner*—Amanda Merlino
*Attorney, Agent, or Firm*—Myers Bigel Sibley & Sajovec, LLP

[57] ABSTRACT

A method for distinguishing live from dead poultry eggs comprises: (a) providing a light source (preferably an infrared light source) and a light detector in opposite facing relation to one another; (b) passing an egg between the light source and light detector; (c) switching the light source at a frequency greater than 100 cycles per second while passing the egg between the light source and the light detector; and (d) detecting light that passes through the egg from the light source with the light detector. Preferably, the egg is passed between the light source and the light detector without making contact therewith. And the method preferably further comprises the step of electronically filtering the signal detected by the light detector to distinguish light emitted from the light source from ambient light. Steps (b) through (d) may be repeated at a rate of at least one egg per second. Apparatus for carrying out the foregoing method is also disclosed.

23 Claims, 7 Drawing Sheets

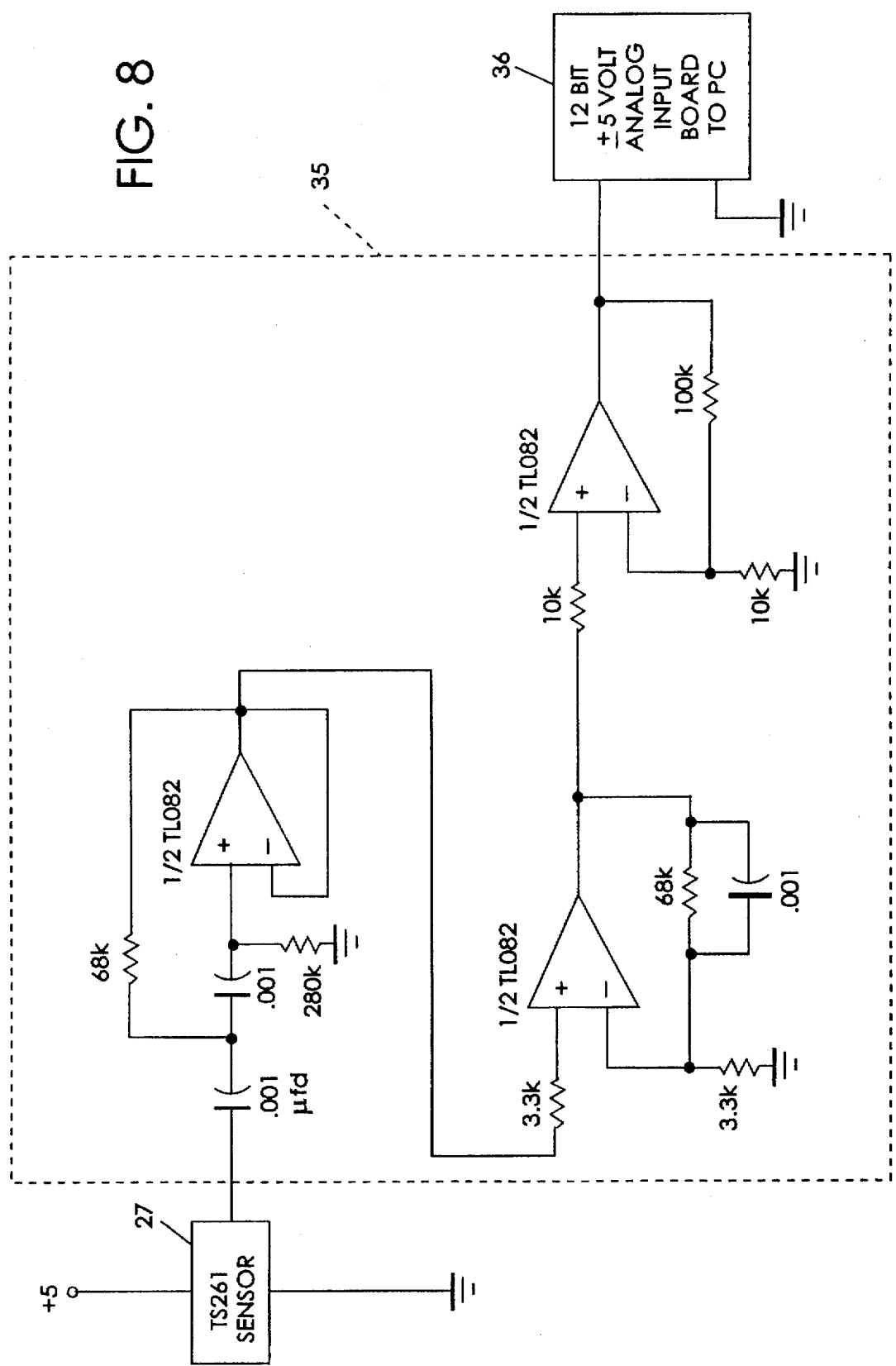

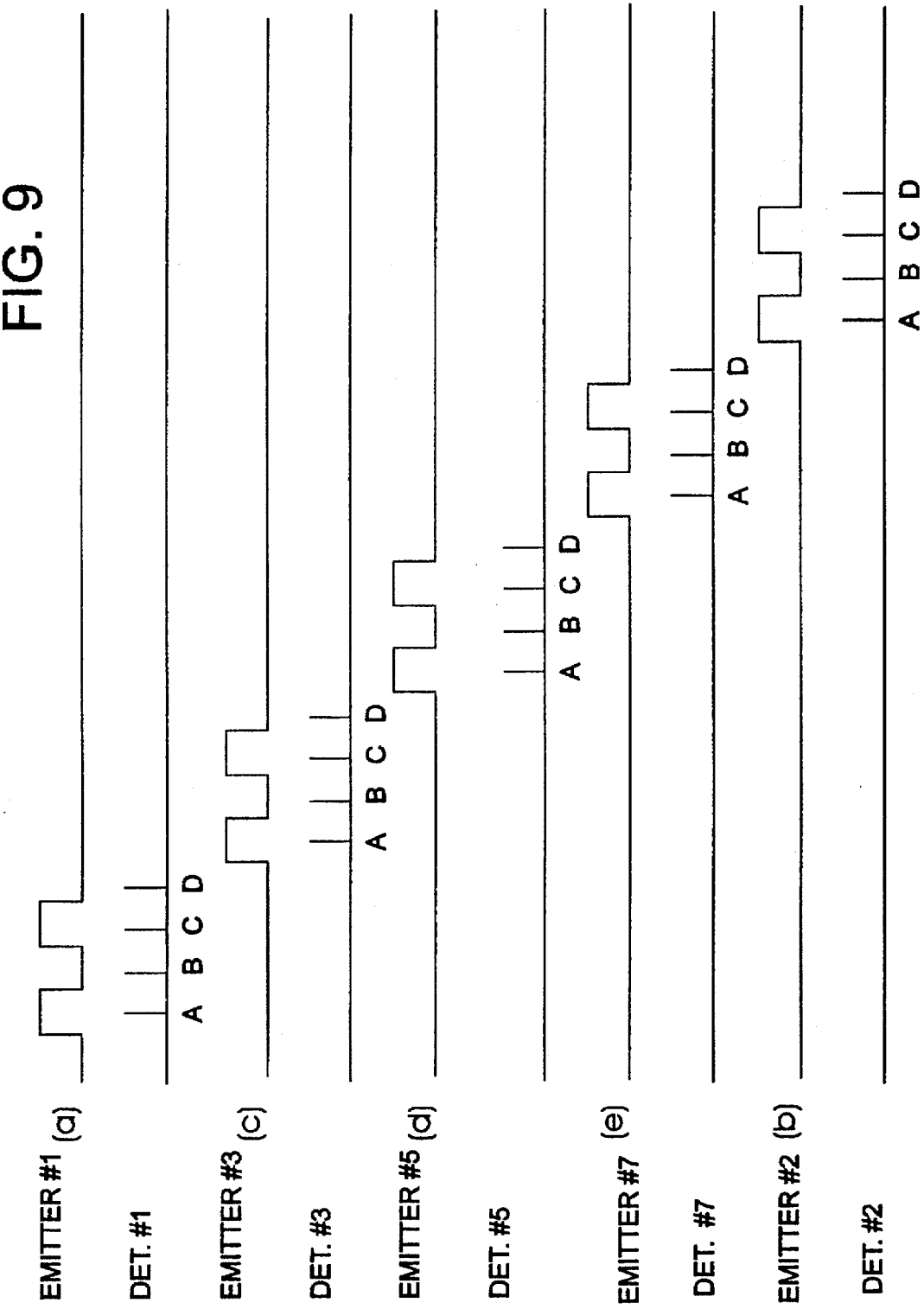

METHOD AND APPARATUS FOR DISTINGUISHING LIVE FROM INFERTILE POULTRY EGGS

FIELD OF THE INVENTION

The present invention concerns methods and apparatus for candling poultry eggs, and in particular concerns methods and apparatus for candling poultry eggs with light that is pulsed or cycled at a frequency different from, and preferably higher than, ambient light.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with poultry eggs, although egg shells appear opaque under most lighting conditions, they are in reality somewhat translucent, and when placed in front of a direct light, the contents of the egg can be observed.

In most practices, the purpose of inspecting eggs, particularly "table eggs" for human consumption, is to identify and then segregate those eggs which have a significant quantity of blood present, such eggs themselves sometimes being referred to as "bloods" or "blood eggs." These eggs are less than desireable from a consumer standpoint, making removal of them from any given group of eggs economically desireable.

U.S. Pat. Nos. 4,955,728 and 4,914,672, both to Hebrank, describe a candling apparatus that uses infrared detectors and the infrared radiation emitted from an egg to distinguish live from infertile eggs.

U.S. Pat. No. 4,671,652 to van Asselt et al. describes a candling apparatus in which a plurality of light sources and corresponding light detectors are mounted in an array, and the eggs passed on a flat between the light sources and the light detectors.

SUMMARY OF THE INVENTION

A first aspect of the present invention is a method for distinguishing live from infertile, including dead, poultry eggs. The method comprises: (a) providing a light source (preferably an infrared light source) and a light detector in opposite facing relation to one another; (b) passing an egg between the light source and light detector; (c) switching the light source at a frequency greater than 100 cycles per second (and preferably at a frequency greater than 200 or 400 cycles per second) while passing the egg between the light source and the light detector; and (d) detecting light that passes through the egg from the light source with the light detector. Preferably, the egg is passed between the light source and the light detector without making contact therewith. The method preferably further comprises the step of electronically filtering the signal detected by the light detector to distinguish light emitted from the light source from ambient light. Steps (b) through (d) may be repeated at a rate of at least one egg per second.

A second aspect of the present invention is an apparatus for distinguishing live from infertile poultry eggs. The apparatus comprises an egg carrier, a light measuring system, and a switching circuit. The light measuring system has a light source (preferably an infrared light source) positioned on one side of the egg carrier and a light detector positioned on the other side of the egg carrier opposite the light source. The switching circuit is operatively associated with the light source for cycling the intensity of the light source at a frequency greater than 100 cycles per second, and preferably at a frequency greater than 200 or 400 cycles per second. The egg carrier is configured to carry the eggs between the light source and the light detector in non-contacting relationship therewith. An electronic filter operatively associated with the light detector is configured to distinguish light emitted from the light source from ambient light (i.e., by filtering out higher and/or lower frequency light signals detected by the detector).

A preferred embodiment may also include an optical filter positioned in front of the light detector for filtering ambient light. A drive system may be operatively associated with the egg carrier, with the drive system configured to pass eggs between the light source and the light detector at a rate of at least 1 egg per second. Typically, the egg carrier is configured to carry at least two rows of eggs in side-by-side relationship to one another; here the apparatus comprises a plurality of the light measuring systems positioned in operative association with each of the rows of eggs, and the switching circuit preferably cycles adjacent ones of the light sources at a time or frequency different from one another. Specifically, pulsing or cycling the light at rates of a thousand or more times per second (typically 2000 times per second) allows measuring all eggs in a row of seven within less than 10 milliseconds, so that moving eggs can be sampled at 0.1 second intervals.

A personal computer or other programmable or non-programmable circuitry may serve as a data collection means operatively associated with the light detectors for storing data associated with the eggs, in which case the switching circuit is operatively associated with the data collection means so that data is collected from each of the light detectors in a cycle corresponding to the cycle of the corresponding light source. Specifically, individual sensors are sampling corresponding emitters that are activated. Furthermore, by taking the difference of successive samples, while a corresponding emitter is on and then off, ambient light can largely be rejected. Rejection of changing ambient light levels, such as from fluorescent lamps, is increased as sampling intervals are made closer in time.

The present invention is explained in greater detail in the drawings herein and the specification set forth below.

BRIEF DESCRIPTION OF THE DRAWINGS

FIG. 8 is a schematic diagram of a light detector and corresponding filter, amplifier and computer input board.

FIG. 9 is a diagram showing the pattern of cycling a row of light emitters and sampling the light detectors. Note that emitter and detector pairs 4 and 6 are not illustrated, but follow the pattern established by emitter and detector pairs 1, 2, 3, 5 and 7. Square pulses on emitter lines indicate times when emitters are active; peaks on detector lines indicate times when detectors are active.

DETAILED DESCRIPTION OF THE PREFERRED EMBODIMENTS

The present invention may be carried out with any types of eggs, including chicken, turkey, duck, geese, quail, and pheasant eggs. Chicken eggs are particularly preferred.

The term "cycled" as used herein refers to the switching of the light source or emitter on and off (for example, fluorescent and incandescent lights on normal house current are said to be cycled at 60 cycles per second, and not to the wavelength of the light itself).

Figure 1:
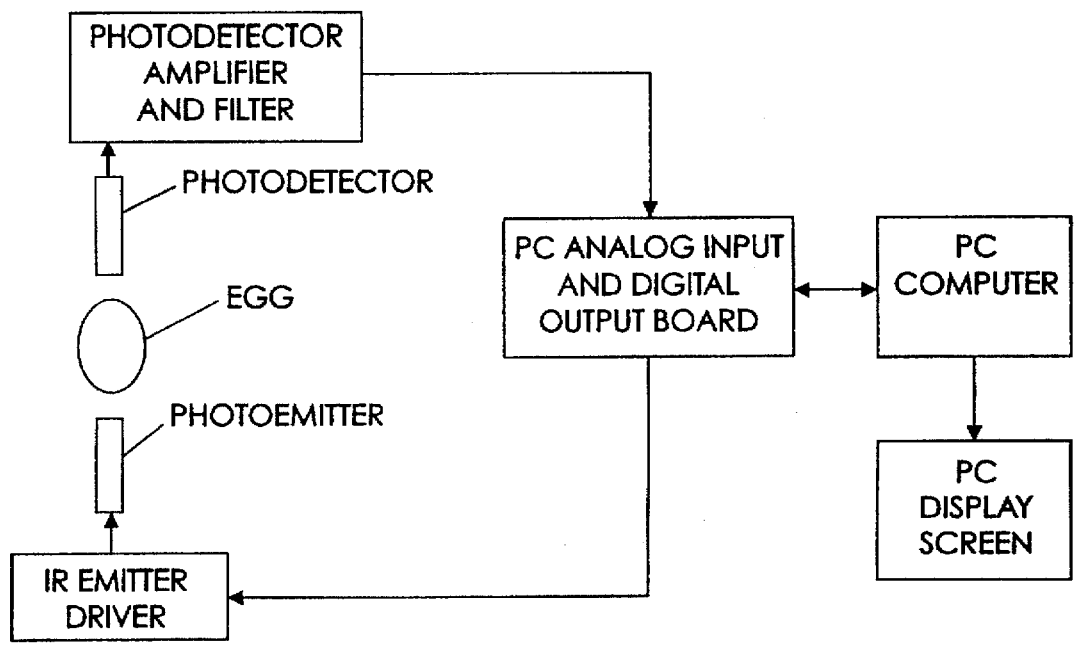
FIG. 1 is a block diagram of a cycled light source control and detector processing for a egg candling in accordance with the present invention.
Figure 2:
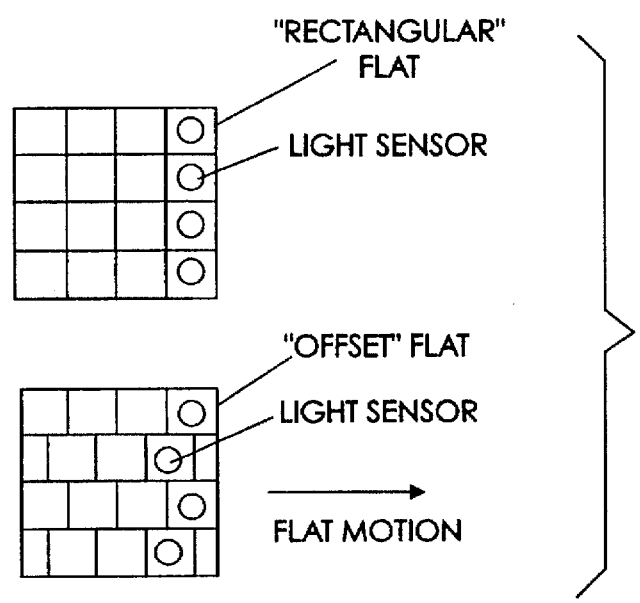
FIG. 2 shows a top view of a rectangular flat of eggs and an offset flat of eggs to be candled by the method of the present invention.

FIGS. 1–2 schematically illustrate apparatus that can be used to carry out the method of the present invention. In overview, with reference to FIG. 1, an apparatus of the invention comprises a photodetector associated with a photodetector amplifier and filter circuit, which is in turn associated with a PC analog input board, and a photoemitter (an infrared emitter) associated with an IR emitter driver circuit, in turn associated with a digital output board. The photoemitter and photodetector are positioned to be on opposite sides of an egg: as illustrated, the photodetector is above and the photoemitter is below the egg, but these positions are not critical and could be reversed, or the emitter and detector placed in a different orientation, so long as light from the emitter illuminates the egg to the detector. The input and output board are installed in a personal computer, with operation of the system monitored on the display screen of the PC computer. In operation, the method of the present invention uses time to allow accurate measurement of the light from a single egg. Light is generated in short bursts from each photoemitter (e.g., 50 to 300 microseconds) and the corresponding photodetector only monitors while it's corresponding photoemitter is operational. To reduce the effect of ambient light, the output of a photodetector when no light is on is subtracted from the reacting when the light is on. A flat of eggs is continuously "scanned" as it moves through the identifier with each detector-source pair active only while at least adjacent, and preferably all other, pairs are quiescent.

As indicated in FIG. 2, the method and apparatus of the invention are particularly adapted for use with "flats" of eggs. Any flat of eggs with rows of eggs therein may be used, and while five rows are illustrated in the two flats shown schematically in FIG. 2, the flat may contain any number of rows, such as seven rows of eggs, with rows of six and seven being most common. Eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat, and the "JAMESWAY 84" flat (in each case, the number indicates the number of eggs carried by the flat).

Figure 3:
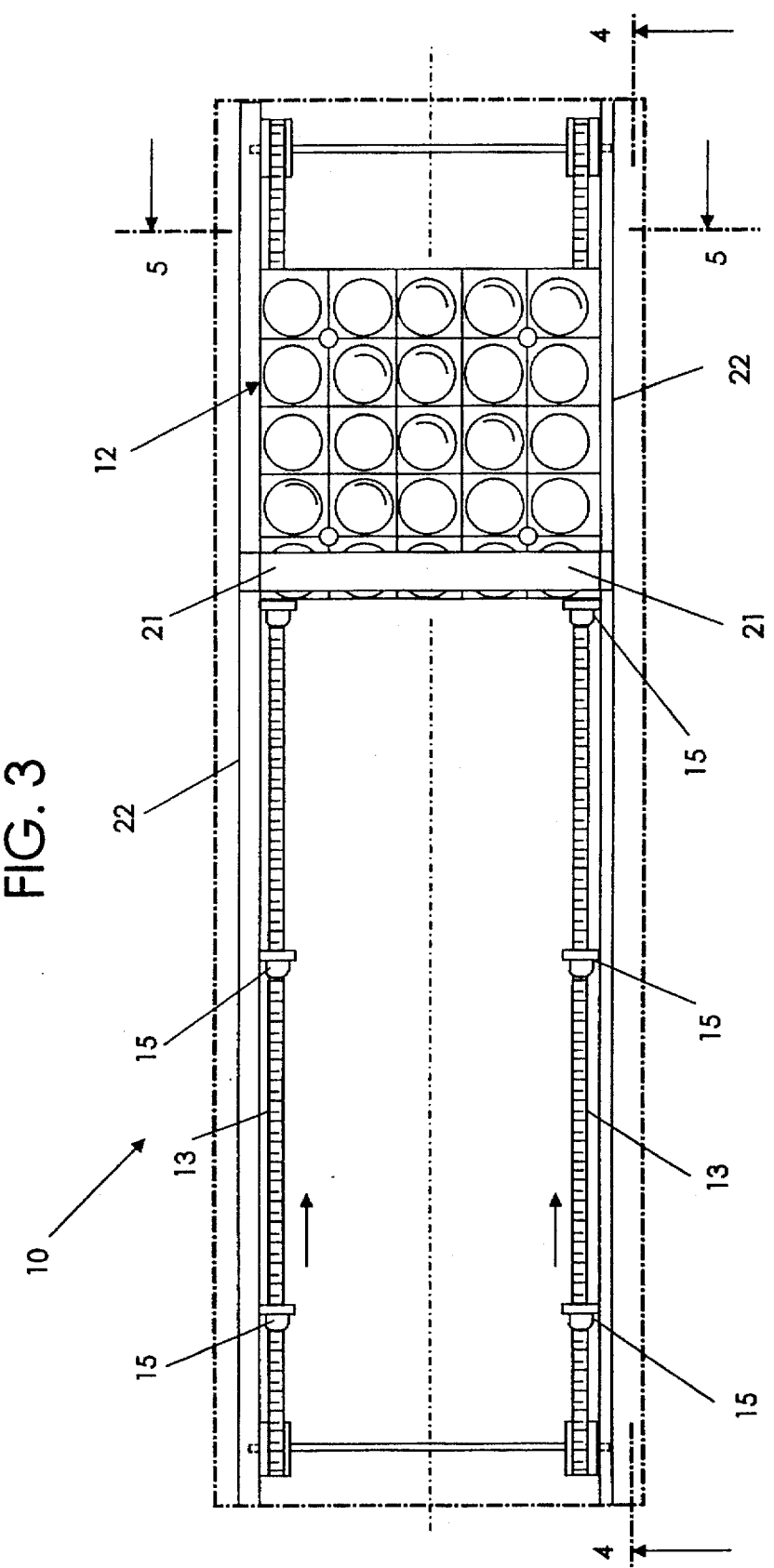
FIG. 3 is a top plan view of an apparatus of the present invention.
Figure 4:
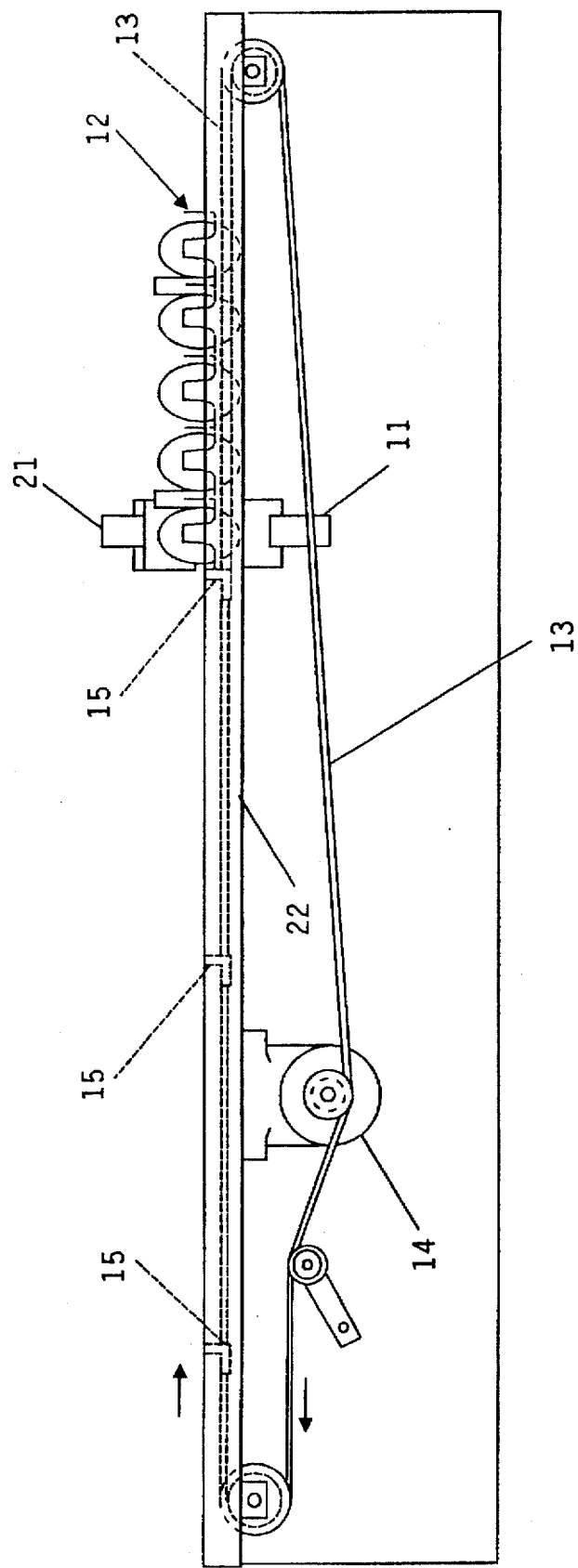
FIG. 4 is an elevational view taken along lines 4—4 of FIG. 3.
Figure 5:
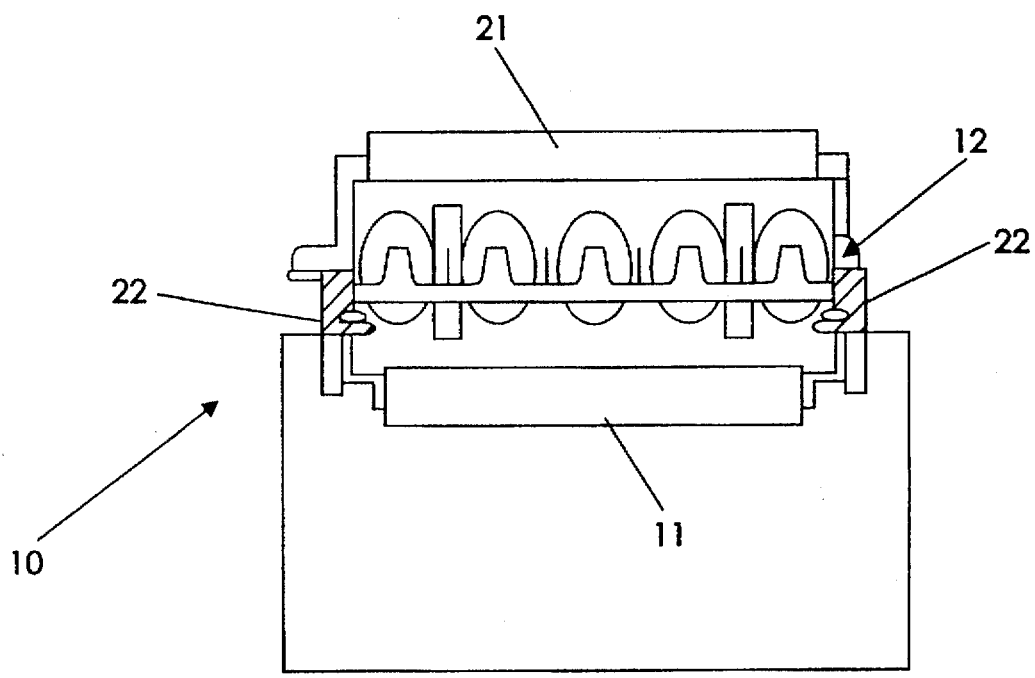
FIG. 5 is an elevational view taken along lines 5—5 of FIG. 3.

FIGS. 3–5 show an apparatus generally designated at 10 that can be used to practice the method of the invention. Apparatus 10 includes an infrared light emitter mounting block 11, an infrared light detector mounting block 21, and a conveyor system as discussed below.

As illustrated, the fixed array of eggs comprises an open bottom setting flat 12 of eggs. The flat 12 carries twenty-five eggs in an array of five rows of five eggs each and rides on a conveyor means which is shown in the form of drive chains 13, chain drive motor 14 and chain drive dogs 15 that moves the flat along the guide rails 22 adjacent the path of the chain 13. In an alternate, preferred embodiment, the chain drive and dogs are replaced with a pair of polymeric conveyor belts riding on support rails, which conveyor belts are ⅜ inch diameter and ride on 0.5 inch frames. Such belts are as found on egg injection equipment, particularly the EMBREX INOVOJECT™ egg injection apparatus, and are desireable for their compatability with operator safety and corrosion resistance. Egg flats are typically moved at rates of 10 to 20 inches per second.

Figure 6:
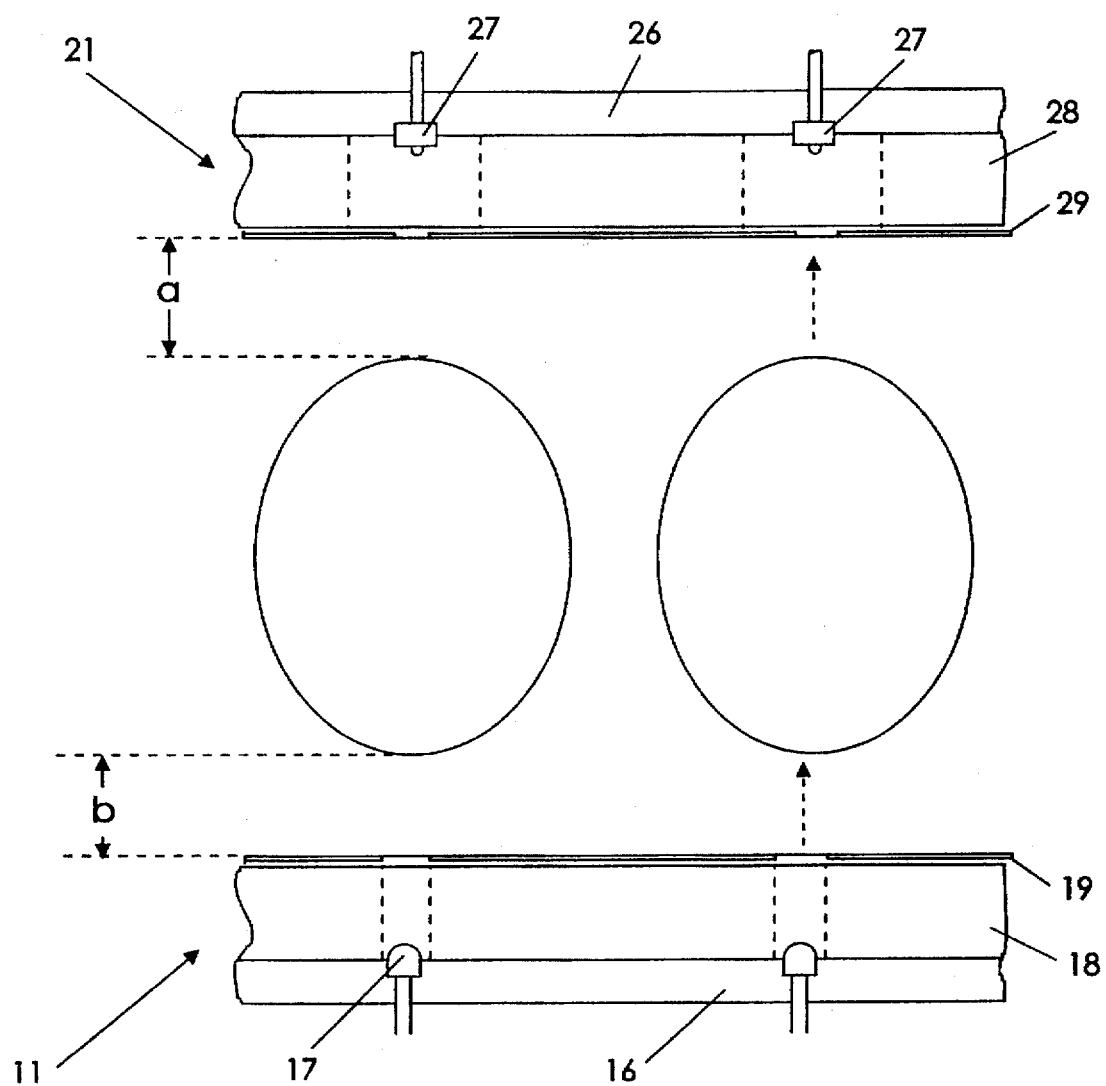
FIG. 6 is a detail view of the light source mounting block and the light detector mounting block.

FIG. 6 illustrates the construction of the infrared light emitter mounting block 11 and the infrared light detector mounting block 21. The infrared light emitter mounting block 11 is comprised of an opaque back plate 16 with the infrared emitters 17 (Photonics Detectors, Inc. Part number PDI-E805) mounted thereto. These emitters include an integral lens, but a non-integral lens system could also be provided for the emitter. These gallium-arsenide light-emitting diodes emit infrared light with a wavelength of 880 nanometers and can be switched on or off with activation times of about one microsecond. An opaque polymer block 18 that is 0.5 inches thick has ¼ inch diameter holes bored therethrough in corresponding relation to each emitter. A 0.040" polycarbonate sheet 19 (opaque except for a 0.25 inch circle above each emitter) overlies block 18. The structure of the mounting block thus provides an optical aperature positioned between the egg and the light emitters 17. In one embodiment, sheets available commercially for overhead projector transparencies are used. Likewise, the infrared light detector mounting block 21 is comprised of an opaque back plate 26 with the infrared detectors 27 (Texas Instruments Part number TSL261) mounted thereto. Integral lenses or non-integral lens systems could optionally be provided with the detectors. An opaque polymer block 28 that is 0.5 inches thick has ¾ inch diameter holes bored therethrough in corresponding relation to each emitter. A 0.040" polycarbonate sheet 29 (opaque except for a 0.25 inch circle above each detector) overlies block 28. The polycarbonate sheets are a light-blocking, infrared-transmissive polymer that have about 90% transmittance of wavelengths between 750 and 2000 nanometers. The infrared light from the emitters has a wavelength near 880 nanometers. Thus, the sheets serve, at least in part, to block and filter ambient light. Again, the structure of the mounting block thus provides an optical aperature positioned between the egg and the light detectors 27. In all cases, opaque materials are is preferably black. The apparatus is configured so that the distance "a" from the top of the egg to the polymer film 29 is from ½ to one inch, and so that the distance "b" from the bottom of the egg to the polymer film 19 is from ½ to one inch, with a distance of 0.5 inches preferred. Note that some egg flats and the variety of egg sizes cause this distance to typically range from ⅜ inch to one inch. The size of the viewed area on the egg is typically a 0.25 to 0.5 inch area. Smaller areas give better rejection of light reflected off of adjacent eggs.

Some of the photoemitters may be offset from the center line of the eggs so that they miss the conveyor belts. It is not necessary that their corresponding detectors be colinearly aligned with the emitters since the light entering the egg is diffused by the shell and contents. In operation, light from the emitter is projected as a 10 degree cone with a total light output in this cone of about 20 milliwatts. Typically the light reaches the egg in a circle about 0.5 inches in diameter and diffuses within the egg so that the entire egg is illuminated and glows. Clear eggs glow with a light level (or irradiance) approximately $10^4$ less than the illuminating irradiance, and live eggs glow with an irradiance about $10^5$ less than the illuminating irradiance.

Figure 7:
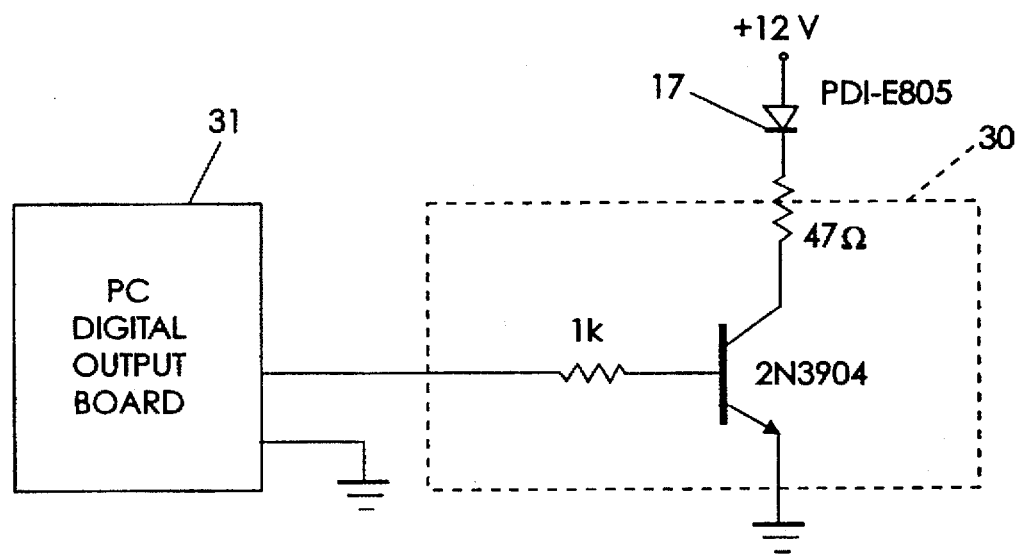
FIG. 7 is a schematic diagram of a computer-driven light source.

FIG. 7 is a schematic diagram of the circuitry 30 corresponding to light source 17, with corresponding digital output board 31 installed in the personal computer (not shown: see FIG. 1), and FIG. 8 is a schematic diagram of the filter, amplifier and input circuitry 35 accompanying light detector 27, with a corresponding 12 bit ±5 volt analog input board 36 installed in the personal computer. All is conventional circuitry, and numerous variations thereon will be readily apparent to those skilled in the art.

In operation of an apparatus as given above, each emitter is typically turned on for about 250 microseconds. The output of each photodetector is amplified by a bandwidth-limited filter (2 kHz high pass filter combined with a 1.0 kHz low pass filter). The filter maximizes detection of the 250 microsecond pulses of light from the photoemitters while minimizing noise from either electronic circuitry or stray light in the environment. The output from each filter is sampled about 120 microseconds after the corresponding emitter is turned on. The samples are digitized and recorded by the computer. A second sample is taken about 25 microseconds after the corresponding emitter is turned off. The off-light sample when subtracted from the on-light sample further improves rejection of ambient lighting around the identifier.

The pattern of cycling the rows of emitters and sampling the detectors is shown in FIG. 9, where:

$Signal_n=(A-B+C-D)/2$ from $detector_n$.

Typically several repetitions of the above process may be done to improve the accuracy of the data from each egg. Eggs pass between the light emitters and detectors on conveyor belts moving about 10 inches per second. At a belt speed of 10 inches per second and a sampling time of 7 milliseconds per row, each egg is scanned every 1/14 of an inch. Two repetitions can be done in about 1000 microseconds, so that, in a row of seven eggs, all seven eggs in a row can be measured in less than 7 milliseconds. After each row is received, software partitions the eggs into live eggs, clear eggs, mid-dead eggs and missing eggs according to the amount of light passed through each egg. The processing begins by establishing that a full row has been received through an algorithm that finds rows by noticing the strong light received by most of the detectors between eggs. Preset cutoffs are used in conjunction with the minimum level of light received by each egg to make a live/dead/mid-dead classification. With clears being greater than 100 millivolts and lives being less than 50 millivolts. After eggs are identified as live, clear, mid-dead or missing, the results are displayed graphically on the PC computer's screen along with cumulative statistics for a group or flock of eggs.

In normal operation, the front edge of an egg flat is located either by the flat moving up to a fixed stop or by a photo-optic device, also operatively associated with the computer, locating the front edge of the flat. Normally the row of illuminators and detectors is aligned with the front row of the flat at that time. The flat is then moved forward by the conveyor system while the row of detectors continuously scan the eggs. Software defines the passage of rows of eggs by the strong light that passes between eggs as the margin between rows moves past the detectors. The minimum light level recorded between successive row edges is used to discriminate clea from live eggs. Data from the entire flat is recorded for later processing to identify mid-dead eggs. As a check on the location of rows, the computer also monitors the condition of the stop (open or closed) as well as the running or stopped state of the conveyor motor.

Eggs identified as clear, dead and/or mid dead can be removed by any conventional method, including manually or by suction-type lifting devices as disclosed in U.S. Pat. No. 4,681,063, the disclosure of which is incorporated by reference herein in its entirety.

The present invention is described in greater detail in the following non-limiting Examples.

EXAMPLE 1

Optical Candling with Cycled Light Source

To illustrate the invention, several chicken eggs were hand candled and then measured by the methodology of the invention. These results are shown in Table 1 below. This data was measured using the 880 nM IR light source and detector. Results show a range of 40 to 83 units for clears, 8 to 25 for mid-deads, and 5.7 to 6 for lives. the significant differences between the three categories of eggs demonstrates the reliable classification eggs possible with the method of the invention.

TABLE 1

| Optical Candling with Cycled Light Source. | | |
|---|---|---|
| Egg Number | Egg Type | Detector Output |
| 1 | clear or early dead | 83 |
| 2 | clear or early dead | 47 |
| 3 | clear or early dead | 98 |
| 4 | clear or early dead | 78 |
| 5 | clear or early dead | 40 |
| 6 | mid dead | 25 |
| 7 | mid dead | 15 |
| 8 | mid dead | 8 |
| 9 | live (day 17) | 6 |
| 10 | live (day 17) | 5.6 |
| 11 | live (day 17) | 6 |
| 12 | live (day 17) | 5.7 |
| 13 | live (day 17) | 5.7 |

The foregoing is illustrative of the present invention, and is not to be construed as limiting thereof. The invention is defined by the following claims, with equivalents of the claims to be included therein.

That which is claimed is:

1. An apparatus for distinguishing live from infertile poultry eggs, comprising:
    an egg carrier;
    a light measuring system having a light source positioned on one side of said egg carrier and a light detector positioned on the other side of said egg carrier opposite said light source; and
    a switching circuit operatively associated with said light source for cycling the intensity of said light source at a frequency greater than 100 cycles per second.

2. An apparatus according to claim 1, wherein said light source is an infrared light source.

3. An apparatus according to claim 1, wherein said egg carrier is configured to carry said eggs between said light source and said light detector in non-contacting relationship therewith.

4. An apparatus according to claim 1, further comprising an aperature positioned in front of said light source.

5. An apparatus according to claim 1, further comprising a lens system positioned in front of said light source.

6. An apparatus according to claim 1, further comprising an aperature positioned in front of said light detector.

7. An apparatus according to claim 1, further comprising a lens system positioned in front of said light detector.

8. An apparatus according to claim 1, further comprising an electronic filter operatively associated with said light detector for distinguishing light emitted from said light source from ambient light.

9. An apparatus according to claim 1, further comprising an optical filter positioned in front of said light detector for filtering ambient light.

10. An apparatus according to claim 1, further comprising a drive system operatively associated with said egg carrier, said drive system configured to pass eggs between said light source and said light detector at a rate of at least 1 egg per second.

11. An apparatus according to claim 1, wherein said egg carrier is configured to carry at least two rows of eggs in side-by-side relationship to one another; and wherein said apparatus comprises a plurality of said light measuring systems positioned in operative association with each of said rows of eggs.

12. An apparatus according to claim 11, wherein said switching circuit cycles adjacent ones of said light sources at a time or frequency different from one another.

13. An apparatus according to claim 11, further comprising data collection means operatively associated with said light detectors for storing data associated with said eggs, and wherein said switching circuit is operatively associated with said data collection means so that data is collected from each of said light detectors in a cycle corresponding to the cycle of the corresponding light source.

14. A method for distinguishing live from infertile poultry eggs, said method comprising:

(a) providing a light source and a light detector in opposite facing relation to one another;

(b) passing an egg between said light source and light detector; and (c) switching said light source at a frequency greater than 100 cycles per second while passing said egg between said light source and said light detector; and (d) detecting light that passes through said egg from said light source with said light detector.

15. A method according to claim 14, wherein said light source is an infrared light source.

16. A method according to claim 14, wherein said egg is passed between said light source and said light detector without making contact therewith.

17. A method according to claim 14, further comprising the step of electronically filtering the signal detected by said light detector to distinguish light emitted from said light source from ambient light.

18. A method according to claim 14, wherein said steps (b) through (d) are repeated at a rate of at least one egg per second.

19. A method for distinguishing live from infertile poultry eggs in a flat of poultry eggs, said flat containing a plurality of rows of eggs, said method comprising:

(a) providing a plurality of pairs of light sources and corresponding light detectors in opposite facing relation to one another;

(b) passing said flat between said light sources and light detectors so that each row in said flat is positioned between a corresponding one pair of said plurality of light sources and light detectors;

(c) activating each of said pairs of light sources and light detectors only when adjacent pairs are inactive;

(d) switching each of said light sources at a frequency greater than 100 cycles per second while said light source is active; and (e) detecting light that passes through each egg in each row of eggs from said corresponding light source with said light detector.

20. A method according to claim 19, wherein each of said light sources is an infrared light source.

21. A method according to claim 19, wherein said eggs are passed between said light sources and said light detectors without making contact therewith.

22. A method according to claim 19, further comprising the step of electronically filtering the signal detected by each of said light detectors to distinguish light emitted from said light source from ambient light.

23. A method according to claim 19, wherein said steps (b) through (e) are repeated at a rate of at least one egg per second.

* * * * *